(12) United States Patent
Saxena et al.

(10) Patent No.: US 8,981,097 B2
(45) Date of Patent: Mar. 17, 2015

(54) INDUSTRIAL PROCESS FOR THE PREPARATION OF BUPRENORPHINE AND ITS INTERMEDIATES

(71) Applicant: Rusan Pharma Limited, Mumbai (IN)

(72) Inventors: Navin Satyapal Saxena, Mumbai (IN); Kunal Saxena, Mumbai (IN); Kaushik Babubhai Sata, Mumbai (IN)

(73) Assignee: Rusan Pharma Limited, Mumbai (IN)

( * ) Notice: Subject to any disclaimer, the term of this patent is extended or adjusted under 35 U.S.C. 154(b) by 0 days.

(21) Appl. No.: 14/302,159

(22) Filed: Jun. 11, 2014

(65) Prior Publication Data

US 2014/0364612 A1    Dec. 11, 2014

(30) Foreign Application Priority Data

Jun. 11, 2013  (IN) .......................... 1988/MUM/2013

(51) Int. Cl.
    *C07D 489/12*    (2006.01)
    *C07D 489/02*    (2006.01)

(52) U.S. Cl.
    CPC .................................. *C07D 489/12* (2013.01)
    USPC .............................................. 546/39; 546/44

(58) Field of Classification Search
    USPC .................................................... 546/39, 44
    See application file for complete search history.

(56) References Cited

U.S. PATENT DOCUMENTS

| 3,433,791 | A | 3/1969 | Bentley |
| 2011/0152527 | A1 | 6/2011 | Patel et al. |
| 2011/0313163 | A1* | 12/2011 | Hudlicky et al. ............... 546/39 |

FOREIGN PATENT DOCUMENTS

WO    2013050748    4/2013

* cited by examiner

*Primary Examiner* — Charanjit Aulakh
(74) *Attorney, Agent, or Firm* — Kramer Amado, P.C.

(57) ABSTRACT

There is provided an efficient industrial process for the preparation of 21-cyclopropyl-7α-(2-hydroxy-3,3-dimethyl-2-butyl)-6,14-endo-ethano-6,7,8,14-tetrahydro-oripavine, i.e. buprenorphine of Formula-I in high yield and purity, with enhanced safety and eco-friendly norms. The invention further relates to an improved process for preparation of intermediates thereof in high yield and purity.

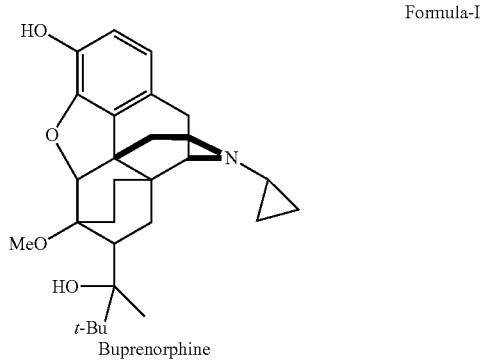

Formula-I

Buprenorphine

17 Claims, No Drawings

INDUSTRIAL PROCESS FOR THE PREPARATION OF BUPRENORPHINE AND ITS INTERMEDIATES

FIELD OF INVENTION

The present invention relates to an efficient industrial process for the preparation of 21-cyclopropyl-7α-(2-hydroxy-3,3-dimethyl-2-butyl)-6,14-endo-ethano-6,7,8,14-tetrahydrooripavine, i.e. buprenorphine of Formula-I, in a high yield and purity with enhanced safety and eco-friendly norms. The invention further relates to an improved process for the preparation of intermediates thereof in a high yield and purity.

BACKGROUND OF THE INVENTION

Buprenorphine, chemically known as 21-cyclopropyl-7α-(2-hydroxy-3,3-dimethyl-2-b 1)-6,14-endo-ethano-6,7,8,14-tetrahydrooripavine, is a semi-synthetic opiate used as a powerful analgesic and is indicated for the treatment of moderate to severe pain and opioid dependence. The compound was first reported by K. W. Bentley in U.S. Pat. No. 3,433,791. This patent reports the semi-synthesis of buprenorphine from thebaine as depicted in Scheme-1.

Scheme-1:

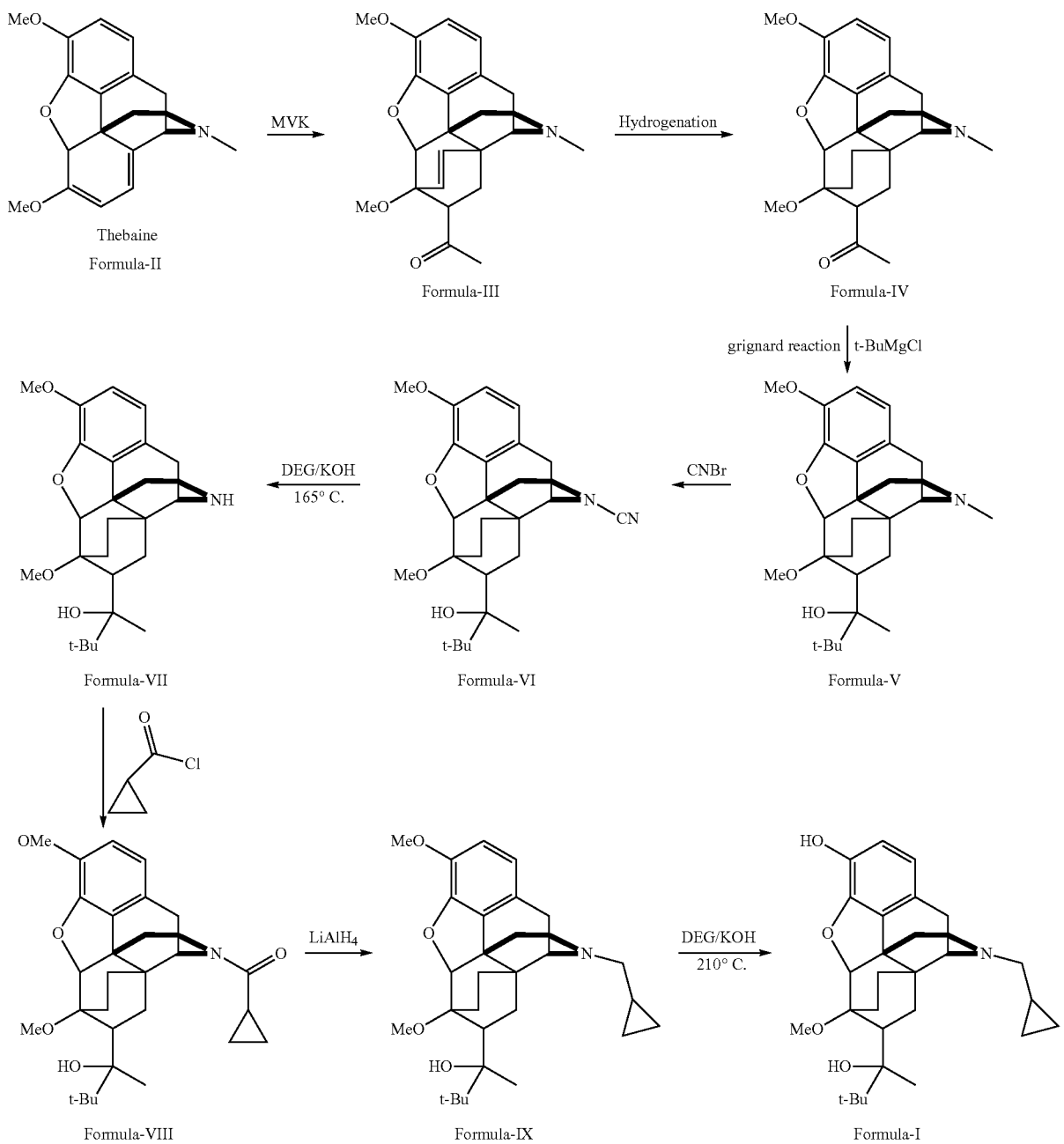

Various methods for the preparation of buprenorphine are reported in the prior art. The following documents disclose methods for preparing buprenorphine wherein thebaine is used as a key starting material.

US 2011/0152527A1 discloses a process for the preparation of buprenorphine as depicted in Scheme-2. The process up to Formula-V is similar to the Bentley process reported in U.S. Pat. No. 3,433,791. However, major modifications yield of the process is only 27% of buprenorphine base from thebaine. In addition, the workup procedure for O-demethylation is tedious and there is no mention of the purity of the product and intermediates. Furthermore, the process uses hazardous, highly flammable and peroxide forming solvents, for example diethyl ether and THF, which makes the process unsuitable at an industrial scale. Finally, the process requires an extra step for purification, resulting in a low yield of the final product.

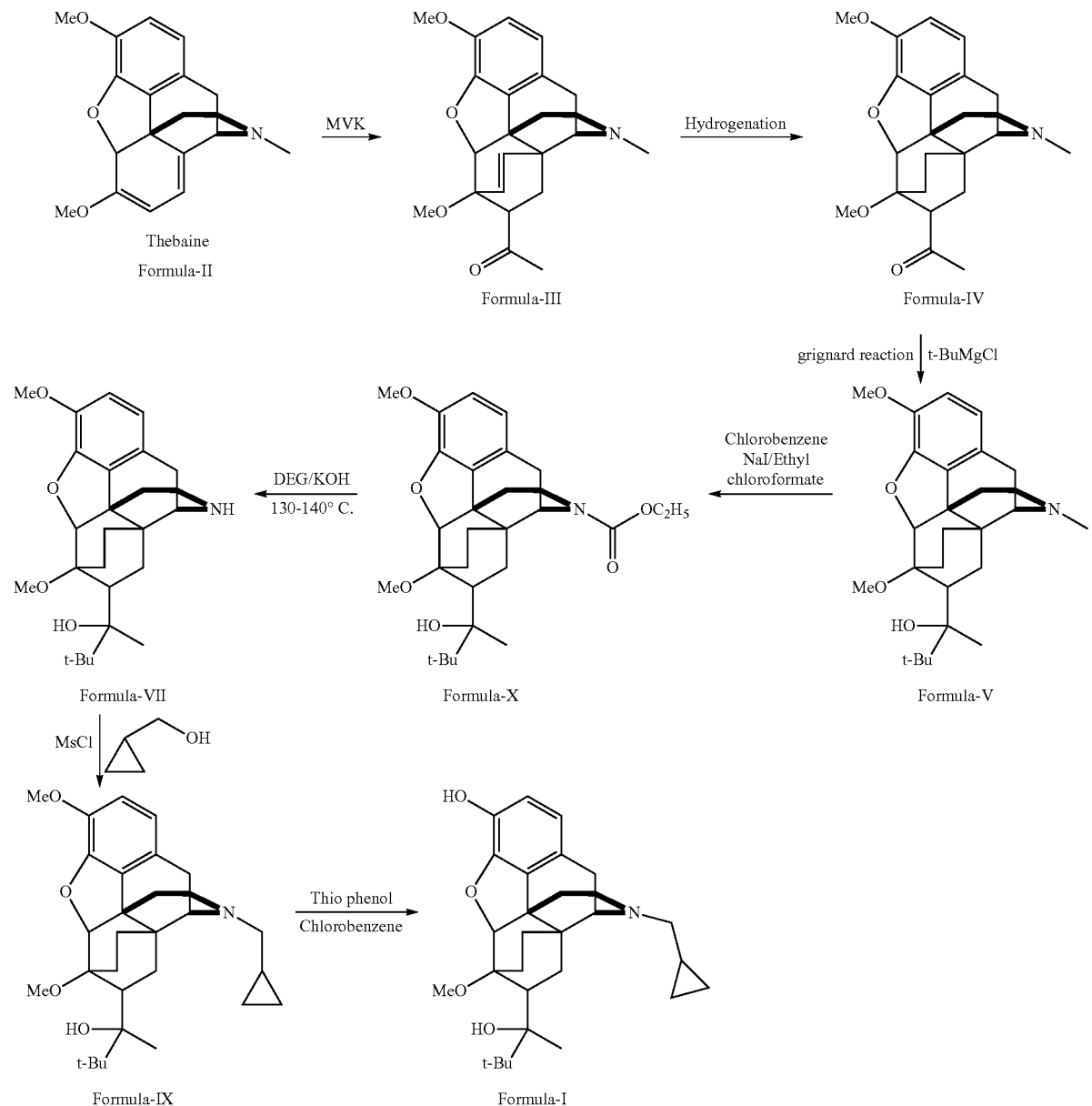

include the use of ethyl chloroformate and then heating at 130° C. to 140° C. with KOH and diethylene glycol for N-demethylation of the compound of Formula-V to get the compound of Formula-VII; the subsequent reaction with cyclopropyl methyl alcohol with mesyl chloride for N-alkylation; and finally the use of thiophenol for O-demethylation to get buprenorphine base of Formula-I. The overall reported WO 2013/050748 of Johnson Matthey PTC discloses a process for the preparation of buprenorphine or its derivatives, as shown in Scheme-3 below. The preparation of the compound of Formula-VI is performed by known processes. However, major modifications include N-demethylation, which is carried out at lower temperatures using NaOH, water and ethylene glycol or methoxy ethanol and then subsequent O-demethylation using a different combination of thiols and bases to get the compound of Formula-XI. This compound is further converted to buprenorphine using methods known in the prior art. The publication does not disclose the formation of compound of Formula-VI and starts with this advance intermediate. The first reaction is N-demethylation, which is followed by 3-O-demethylation to get the compound of Formula-XI which is further converted to buprenorphine. A disadvantage associated with this process is the formation of impurities which arises during the final step of N-alkylation, as alkylation can occur on both the NH group and 3-phenolic group. Thus, additional steps for purification may be required, which lead to poor yield and lower quality of the final product. It is further mentioned that 3-O-demethylation cannot happen on the N-alkylcycloalkylated intermediate. For that reason, both N-demethylation and O-demethylation are carried out prior to the N-alkylation step.

Scheme-3:

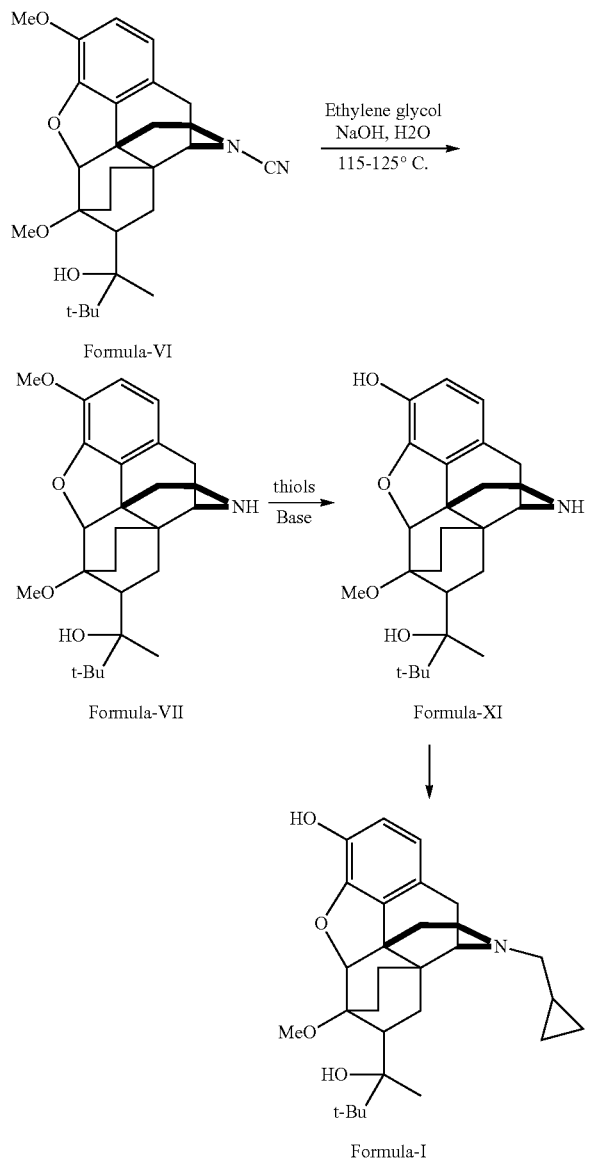

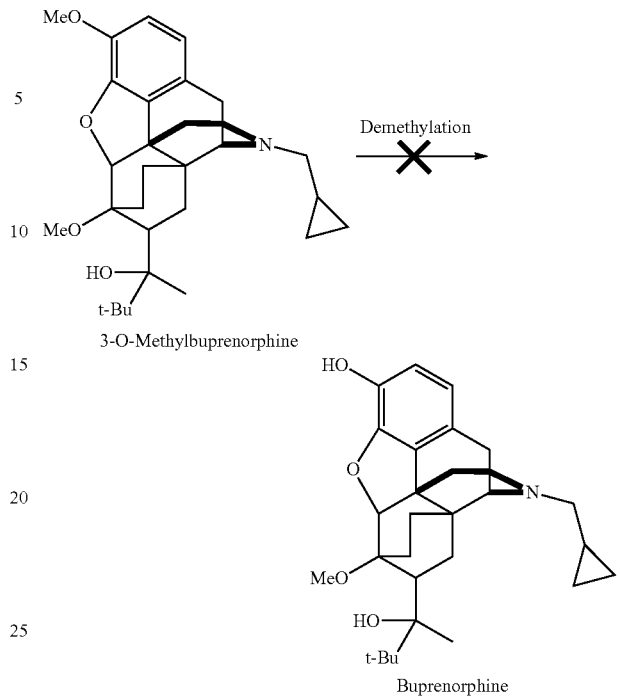

One drawback associated with the prior art processes is an overall low yield of product buprenorphine. Another drawback associated with the prior art processes is the use of toxic, highly flammable and hazardous solvents in the Grignard reaction step, for example benzene, diethyl ether and THF, making the process unsuitable for scaling-up to industrial scale due to safety and environmental concerns. Additionally, the prior art processes are prone to the formation of by-products/impurities and thus, require extra steps for purification at intermediate stages as well as at the final product stage. This leads to poor yield and inferior quality at intermediate stages as well as at the final product stage. It is clearly mentioned in WO 2013/050748 that when the amino group is substituted with an -alkylcycloalkyl group, such as methyl cyclopropane, the 3-O-demethylation reaction does not work efficiently. The attempted O-demethylation of 3-O-methyl buprenorphine (N-alkylated) gives a conversion to buprenorphine of no more than 2.1% using potassium tert.butoxide and 1-dodecanethiol. The same reaction when attempted using sodium propane thiolate was unsuccessful and no product was detected.

Thus, there remains a need in the art to provide an efficient, industrially scalable process for the conversion of thebaine to buprenorphine and the intermediates thereof, in a high yield and purity.

Further to this, there remains a need in the art to reduce the number of solvents used in the process for preparing buprenorphine and the intermediates thereof, in order to render the process economically viable.

SUMMARY OF THE INVENTION

The present invention provides technical solutions to overcome the drawbacks of the prior art processes for the preparation of buprenorphine and its intermediates, in particular those disclosed above in Scheme-2 and 3.

According to a first aspect of the present invention, there is provided a process for the preparation of a compound of Formula-I, comprising:

Formula-I

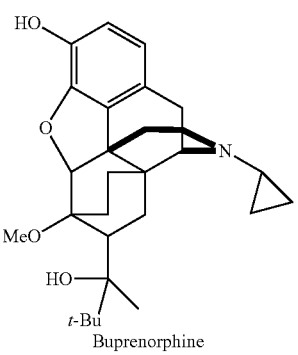

Buprenorphine a) contacting thebaine of Formula-II, (5α)-6,7,8,14-tetrahydro-4,5-epoxy-3,6-dimethoxy-17-methylmorphinan, with methyl vinyl ketone in a solvent to obtain a compound of Formula-III, 7α-acetyl-6,14-endo-etheno-6,7,8,14-tetrahydrothebaine (TA);

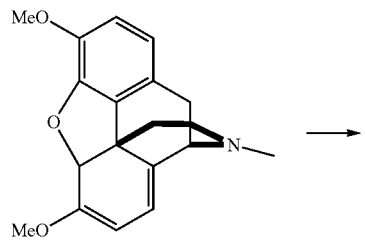

Thebaine
Formula-II

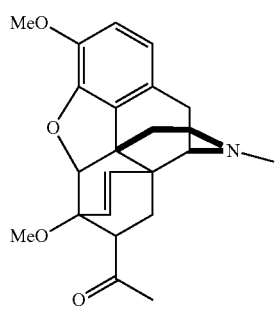

TA
Formula-III b) reducing the compound of Formula-III obtained in step (a) by catalytic hydrogenation or by catalytic transfer hydrogen reaction in a solvent to obtain a compound of Formula-IV, 7α-acetyl-6,14-endo-ethano-6,7,8,14-tetrahydrothebaine (TAR);

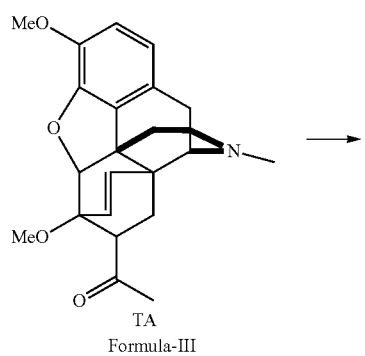

TA
Formula-III

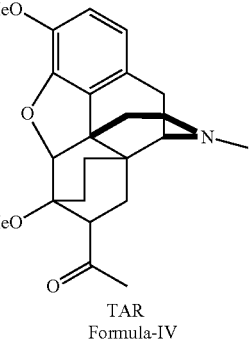

TAR
Formula-IV c) contacting the compound of Formula-IV obtained in step (b) with tertiary butyl metal halide in a solvent to obtain a compound of Formula-V, 7α-(2-hydroxy-3,3-dimethyl-2-butyl)-6,14-endo-ethano-6,7,8,14-tetrahydrothebaine (TARG);

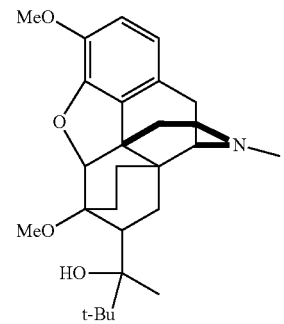

TAR
Formula-IV

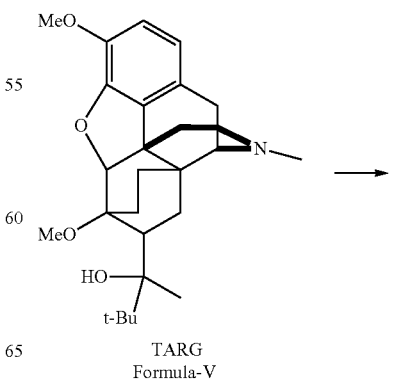

TARG
Formula-V d) contacting the compound of Formula-V obtained in step (c) with cyanogen bromide in a solvent to yield a compound of Formula-VI, N-cyano-7α-(2-hydroxy-3,3-dimethyl-2-butyl)-6,14-endo-ethano-6,7,8,14-tetrahydronorthebaine (TARG-NCN);

TARG
Formula-V

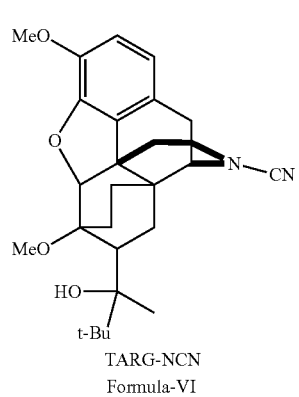

TARG-NCN
Formula-VI

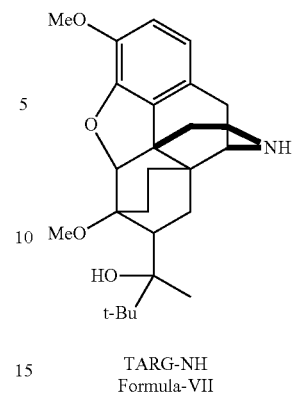

TARG-NH
Formula-VII e) contacting the compound of Formula-VI obtained in step (d) with alkali metal hydroxide in a solvent to obtain a compound of Formula-VII, 7α-(2-hydroxy-3,3-dimethyl-2-butyl)-6,14-endo-ethano-6,7,8,14-tetrahydronorthebaine (TARG-NH);

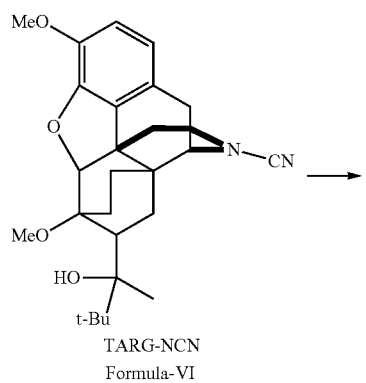

TARG-NCN
Formula-VI

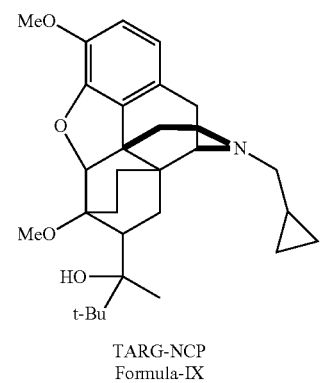

TARG-NCP
Formula-IX g) contacting the compound of Formula-IX obtained in step (f) with an alkane thiol and a base in a solvent to produce a compound of Formula-I

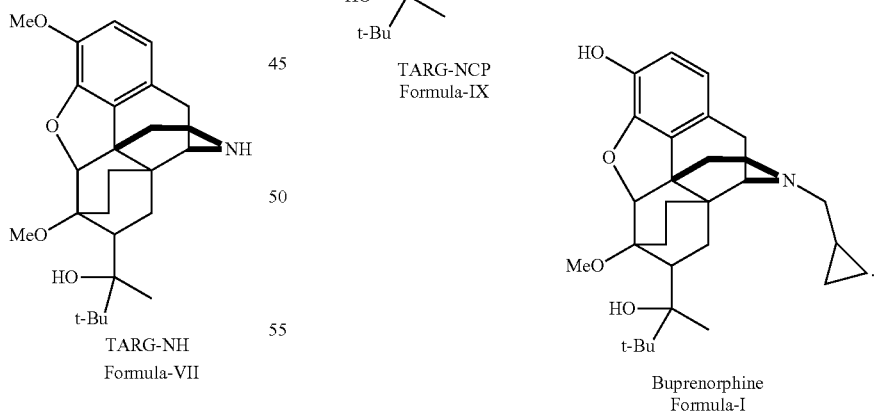

TARG-NH
Formula-VII

TARG-NCP
Formula-IX

Buprenorphine
Formula-I f) contacting the compound of Formula-VII obtained in step (e) with cyclopropyl methyl-L in a solvent to produce a compound of Formula-IX, N-cyclopropylmethyl-7α-(2-hydroxy-3,3-dimethyl-2-butyl)-6,14-endo-ethano-6,7,8,14-tetrahydronorthebaine (TARG-NCP), wherein L- is a leaving group selected from halides, tosyl and mesyl; and The invention provides an efficient, economical and industrially viable process for the preparation of 21-cyclopropyl-7α-(2-hydroxy-3,3-dimethyl-2-butyl)-6,14-endo-ethano-6,7,8,14-tetrahydrooripavine i.e. buprenorphine of Formula-I, in a high yield and purity. Additionally, the invention provides an in-situ process for the preparation of buprenorphine (Formula-I) and its intermediate compound of Formula-VI, thus reducing the number of operational steps.

According to a second aspect of the present invention, there is provided a process for the preparation of a compound of Formula-V, comprising contacting a compound of Formula-IV with tertiary butyl metal halide in CPME.

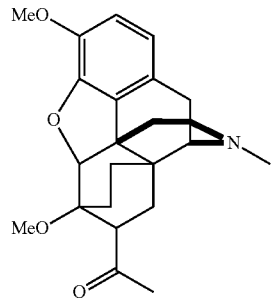

TAR
Formula-IV

→

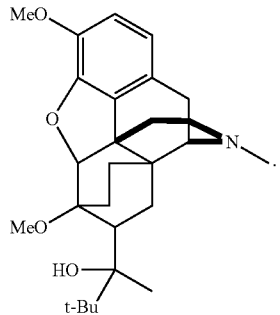

TARG
Formula-V

Advantageously, the process results in the formation of the compound of Formula-V in a higher yield and purity compared to the prior art processes. Additionally, the process uses a safe and eco-friendly solvent, namely CPME.

According to a third aspect of the present invention, there is provided an in-situ process for the preparation of a compound of Formula-VI, comprising contacting a compound of Formula-IV with tertiary butyl metal halide in CPME to obtain a compound of Formula-V, followed by reaction with cyanogen bromide to obtain a compound of Formula-VI, without isolating the compound of Formula-V:

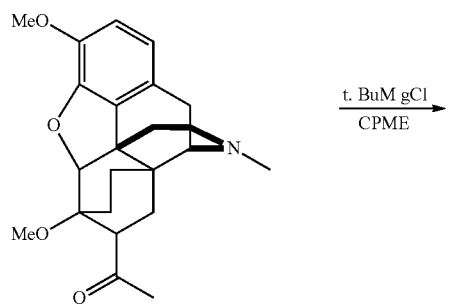

TAR
Formula-IV $\xrightarrow{\text{t. BuMgCl}}{\text{CPME}}$

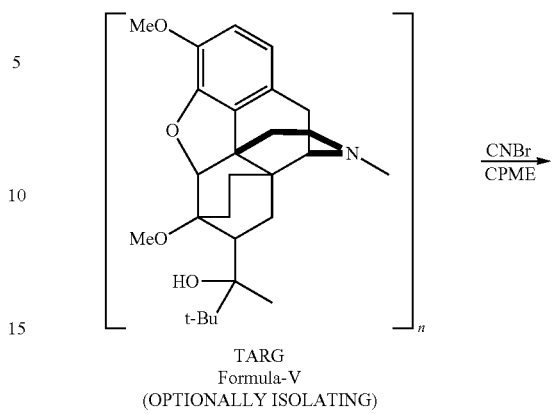

TARG
Formula-V
(OPTIONALLY ISOLATING)

$\xrightarrow{\text{CNBr}}{\text{CPME}}$

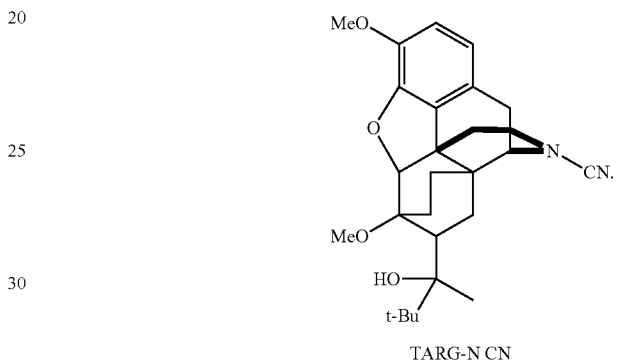

TARG-N CN
Formula-VI

Advantageously, the process results in the formation of the compound of Formula-VI in a higher yield and purity compared to the prior art processes. Additionally, the process uses a safe and eco-friendly solvent. Furthermore, due to the in-situ nature of the process, fewer operational steps are required to form the compound of Formula-VI.

According to a fourth aspect of the present invention, there is provided a process for the preparation of a compound of Formula-IX, comprising contacting a compound of Formula-VII with cyclopropyl methyl halide in the presence of an acid scavenger in a solvent selected from acetonitrile and CPME, to obtain a compound of Formula-IX:

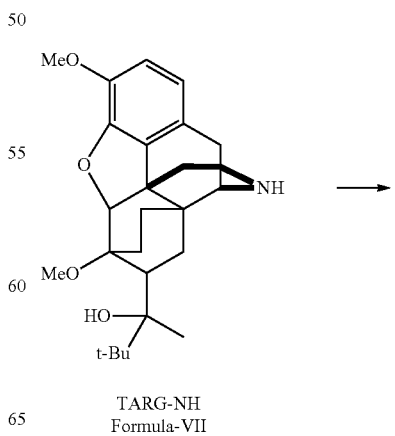

TARG-NH
Formula-VII

→

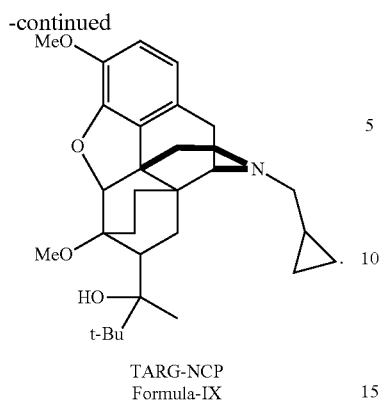

TARG-NCP
Formula-IX

Advantageously, the process results in the formation of the compound of Formula-IX in a higher yield and purity compared to the prior art processes. Additionally, the process uses a safe and eco-friendly solvent.

DEFINITIONS

Thebaine: (5α)-6,7,8,14-Tetrahydro-4,5-epoxy-3,6-dimethoxy-17-methylmorphinan.
TA: 7α-Acetyl-6,14-endo-etheno-6,7,8,14-tetrahydrothebaine
TAR: 7α-Acetyl-6,14-endo-ethano-6,7,8,14-tetrahydrothebaine
TARG: 7α-(2-Hydroxy-3,3-dimethyl-2-butyl)-6,14-endo-ethano-6,7,8,14-tetrahydrothebaine
TARG-NCN: N-Cyano-7α-(2-hydroxy-3,3-dimethyl-2-bl)-6,14-endo-ethano-6,7,8,14-tetrahydronorthebaine
TARG-NH: 7α-(2-Hydroxy-3,3-dimethyl-2-butyl)-6,14-endo-ethano-6,7,8,14-tetrahydronorthebaine.
TARG-NCP: N-Cyclopropylmethyl-7α-(2-hydroxy-3,3-dimethyl-2-butyl)-6,14-endo-ethano-6,7,8,14-tetrahydronorthebaie.
DMF: dimethyl formamide
DMSO: dimethyl sulfoxide
THF: tetrahydrofuran
CPME: cyclopentyl methyl ether
DMPU: dimethyl propylene urea
DMA: dimethyl acetamide
NMP: N-methylpyrrolidinone
DEA: diethyl acetamide
MVK: methyl vinyl ketone
DEF: diethyl formamide
DEG: diethylene glycol
MtBE: methyl tertiary butyl ether
MsCl: mesyl chloride
ACN: acetonitrile
PSI: pounds per square inch

DETAILED DESCRIPTION OF THE INVENTION

The invention will now be described in detail in connection with certain preferred and optional embodiments, so that various aspects thereof may be more fully understood and appreciated.

The term 'contacting' as used herein refers to mixing, heating, stirring, refluxing or combinations thereof.

The present invention discloses an efficient, economical and industrially viable process for the preparation of buprenorphine of Formula-I. The present invention further discloses processes for the preparation of its intermediates of Formula-V, VI and IX.

According, to a first aspect of the present invention, there is provided a process for the preparation of buprenorphine of Formula-I, comprising:

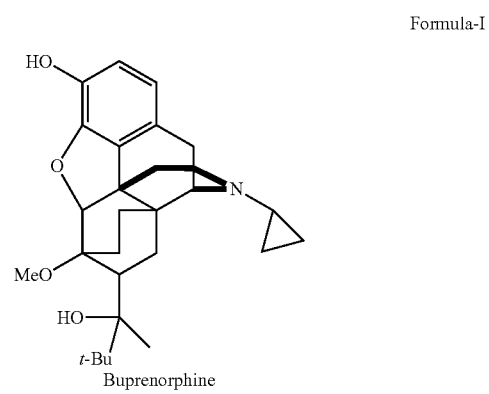

Formula-I

Buprenorphine a) contacting thebaine of Formula-II, (5α)-6,7,8,14-tetrahydro-4,5-epoxy-3,6-dimethoxy-17-methylmorphinan, with methyl vinyl ketone (MVK) in a solvent to obtain a compound of Formula-III, 7α-acetyl-6,14-endo-etheno-6,7,8,14-tetrahydrothebaine (TA);

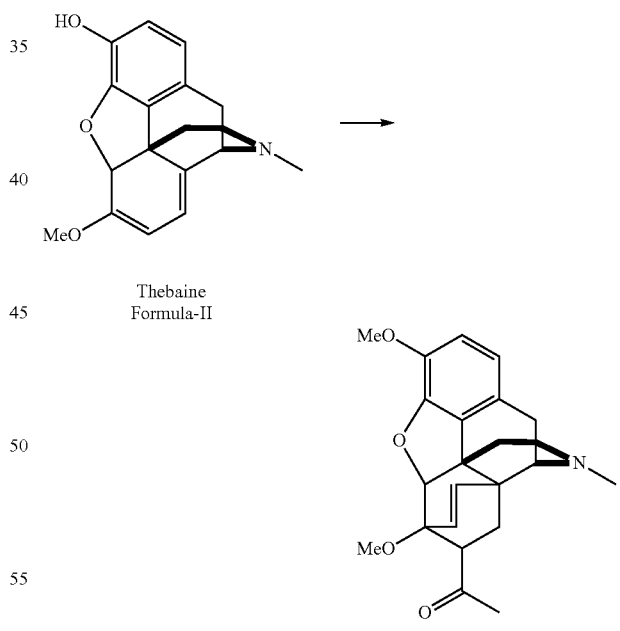

Thebaine
Formula-II

TA
Formula-III b) reducing 7α-acetyl-6,14-endo-etheno-6,7,8,14-tetrahydrothebaine (TA) of Formula-III obtained in step (a) by catalytic hydrogenation or by catalytic transfer hydrogen reaction in a solvent to obtain a compound of Formula-IV, 7α-acetyl-6,14-endo-ethano-6,7,8,14-tetrahydrothebaine (TAR);

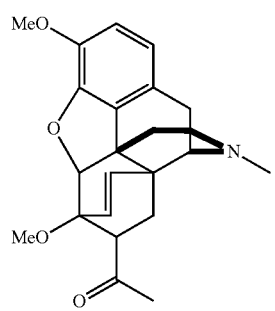

TA
Formula-III

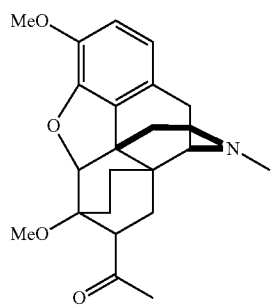

TAR
Formula-IV c) contacting the compound of Formula-IV obtained in step (b) with a tertiary butyl metal halide (t-BuMX) in a solvent to obtain a compound of Formula-V, 7α-(2-hydroxy-3,3-dimethyl-2-butyl)-6,14-endo-ethano-6,7,8,14-tetrahydrothebaine (TARG);

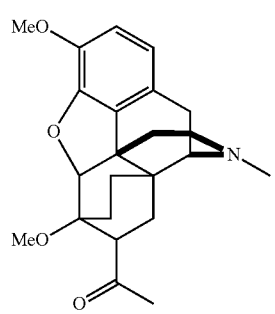

TAR
Formula-IV d) contacting the compound of Formula-V obtained in step (c) with cyanogen bromide in a solvent to yield a compound of Formula-VI, N-cyano-7α-(2-hydroxy-3,3-dimethyl-2-butyl)-6,14-endo-ethano-6,7,8,14-tetrahydronorthebaine (TARG-CN);

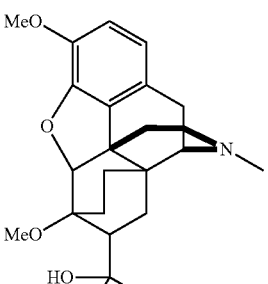

TARG
Formula-V

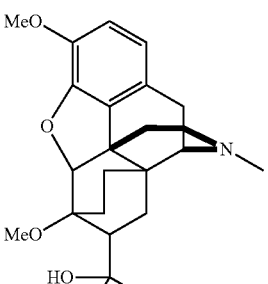

TARG-NCN
Formula-VI e) contacting the compound of Formula-VI obtained in step (d) with alkali metal hydroxide in a solvent to obtain a compound of Formula-VII 7α-(2-hydroxy-3,3-dimethyl-2-butyl)-6,14-endo-ethano-6,7,8,14-tetrahydronorthebaine (TARG NH);

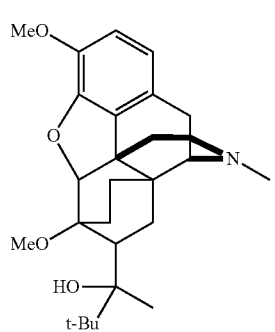

TARG
Formula-V

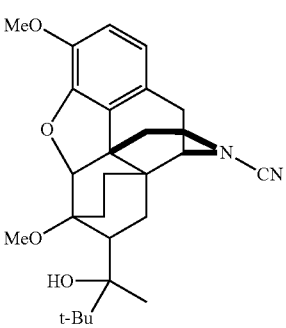

TARG-NCN
Formula-VI

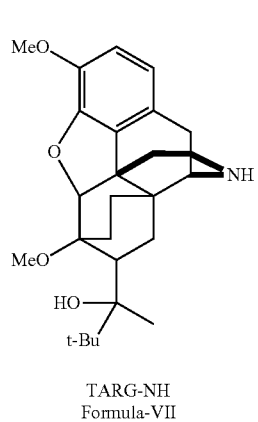

TARG-NH
Formula-VII

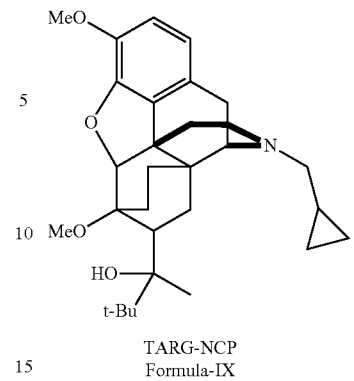

TARG-NCP
Formula-IX

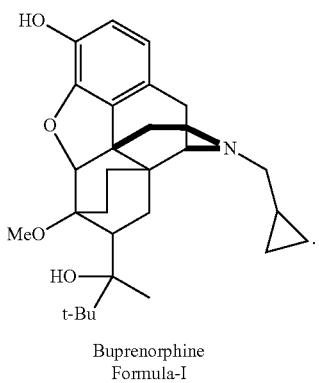

Buprenorphine
Formula-I f) contacting the compound of Formula-VII obtained in step (e) with cyclopropyl methyl-L in a solvent to produce a compound of Formula-IX, N-cyclopropylmethyl-7α-(2-hydroxy-3,3-dimethyl-2-butyl)-6,14-endoethano-6,7,8,14-tetrahydronorthebaine (TARG NCP), wherein L is a leaving group selected from halides, tosyl and mesyl; and

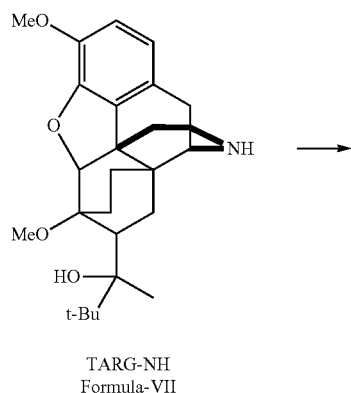

TARG-NH
Formula-VII

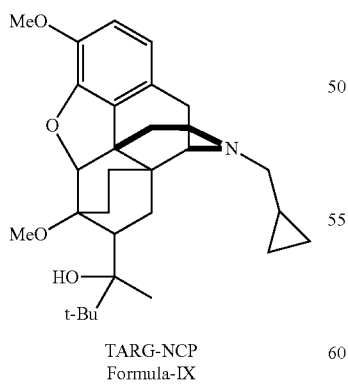

TARG-NCP
Formula-IX g) contacting the compound of Formula-IX obtained in step (f) with an alkanethiol and a base in a solvent to produce a compound of Formula-I (buprenorphine)

Detailed Process Steps are Outlined Below:

Step (a): Preparation of TA (Formula-III) from Thebaine:

Thebaine of Formula-II is contacted with methyl vinyl ketone (MVK) in the presence of a solvent to produce the compound of Formula-III.

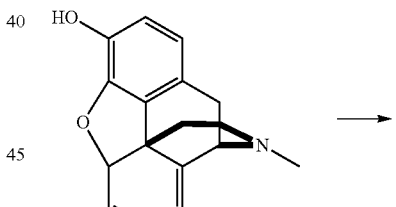

Thebaine
Formula-II

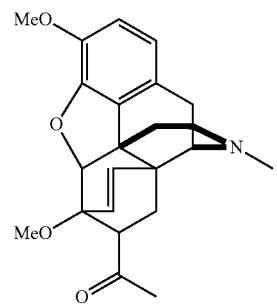

TA
Formula-III

Preferably methyl vinyl ketone is used in the ratio of 0.5 volume to Thebaine. The solvent used in this step may be selected from inert organic solvents, including aromatic hydrocarbons, for example toluene and xylene, and ethereal solvents, for example THF, Me-THF, methyl tert.butyl ether and cyclopentyl methyl ether. Preferably the solvent is cyclopentyl methyl ether.

Step (h): Hydrogenation to Prepare TAR (Formula-IV):

Step (b) involves the preparation of the intermediate of Formula-IV (TAR) by reducing the double bond of the thebaine adduct (TA) of Formula-III. Preferably this step is carried out in the presence of a protic or aprotic solvent at a temperature in the range of from 80° C. to 85° C. and a pressure of 100 PSI. Under these conditions, the yield and purity of the compound of Formula-IV is enhanced.

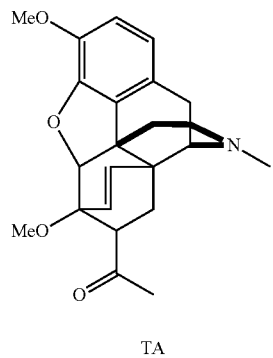

TA
Formula-III

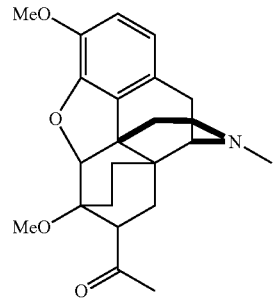

TAR
Formula-IV

The reduction is carried out by catalytic transfer hydrogen reaction or by catalytic hydrogenation.

The catalytic hydrogen transfer reaction preferably takes place in the presence of ammonium formate, formic acid or hydrazine hydrate in the presence of a protic or aprotic solvent at atmospheric pressure. This is advantageous since it avoids using an external source of hydrogen gas and increased pressure.

The catalytic hydrogenation reaction may take place in the presence of a heterogeneous catalyst and a protic or aprotic solvent. The heterogeneous catalyst for catalytic hydrogenation may be selected from metals such as Palladium and Platinum, loaded onto carbon, barium sulphate, $Pt_2O$ or Raney nickel for example. Preferably the heterogeneous catalyst is 10% palladium loaded onto carbon. The reaction is preferably carried out at a temperature of from 80° C. to 85° C. and under hydrogen pressure of 100 PSI. The protic or aprotic solvent may be selected from $C_1$ to $C_5$ alcohols, organic acids, esters, ethers and mixtures thereof.

Step (c): Grignard Reaction for Preparation of TARG (Formula-V):

Step (c) involves the preparation of the buprenorphine intermediate of Formula-V, comprising reacting a Grignard reagent with the compound of Formula-IV (TAR) to produce the compound of Formula-V (TARG). The Grignard reagent may be prepared by the reaction of magnesium, lithium, zinc, cadmium metal or derivatives thereof, with a tertiary butyl halide, where the halide may be selected from chloride, bromide or iodide. Preferably the Grignard reagent is t-BuMgCl, t-BuMgBr or t-BuMgI.

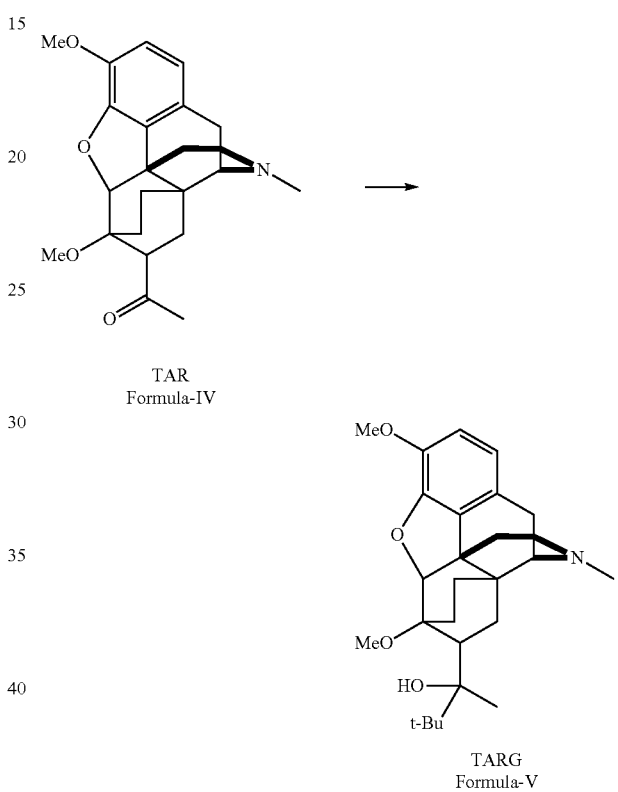

TAR
Formula-IV

TARG
Formula-V

Step (c) is carried out in the presence of a solvent. Examples of suitable solvents include, but are not limited to, ethereal solvents, for example dialkyl ether, wherein the alkyl is selected from $C_1$ to $C_4$ straight or branched chain alkyl groups e.g. diethyl ether, THF, 2-methyl THF, methyl tert-butyl ether, dimethoxy ethane, cyclopentyl methyl ether and diisopropyl ether; dioxanes; dialkoxy ethanes; and aliphatic or aromatic hydrocarbons, for example toluene, hexane, heptane, cyclohexane or mixtures thereof. Preferably the solvent is cyclopentyl methyl ether. The particular use of an eco-friendly solvent such as cyclopentyl methyl ether in this step makes the process commercially viable on an industrial scale.

Step (d) and Step (e): N-demethylation to Prepare TARG-NH (Formula-VII):

Step (d) involves the reaction of the compound of Formula-V with cyanogen bromide in a solvent to produce the compound of Formula-VI (TARG-NCN). Step (e) involves the compound of Formula-VI being reacted with a base in a solvent to yield the buprenorphine intermediate of Formula-VII.

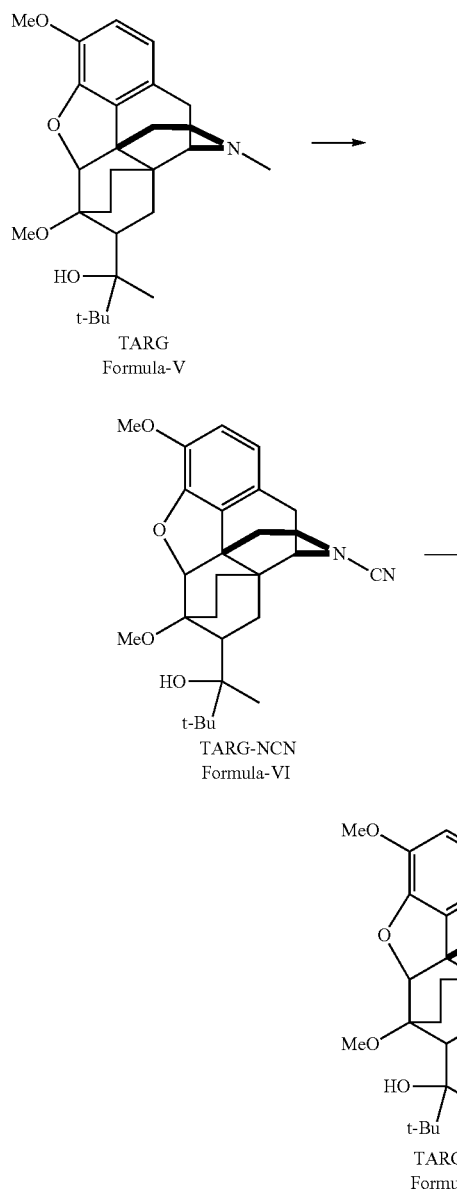

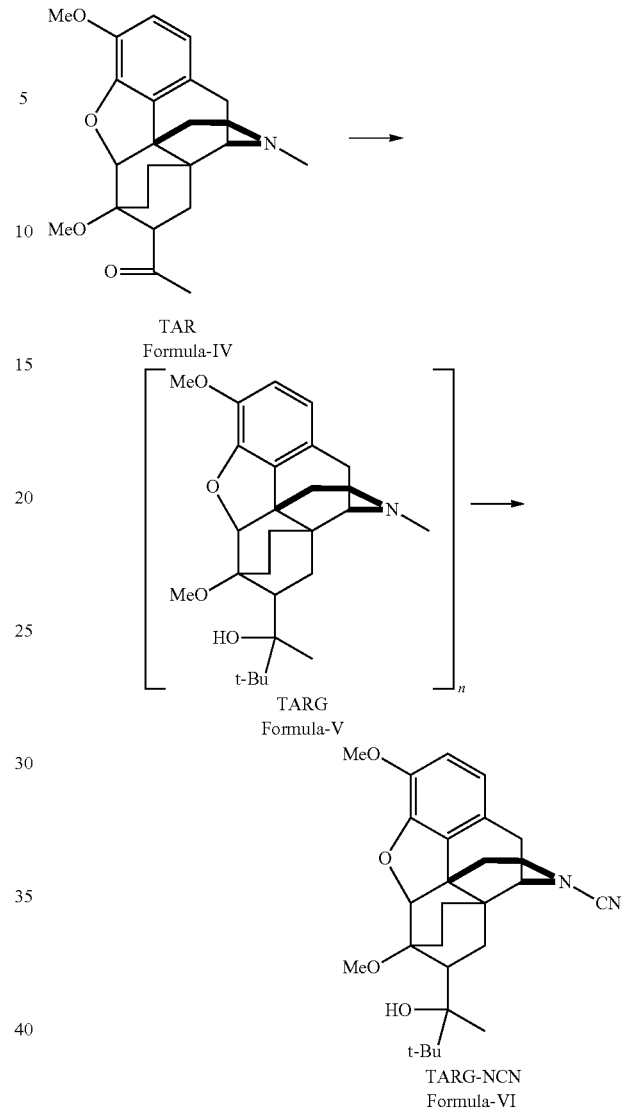

There is no particular restriction on the nature of the solvent to be employed for the formation of the compound of Formula-VI in step (d), provided that it has no adverse effect on the reaction or the reagents involved. Examples of suitable solvents include, but are not limited to, ethereal solvents for example diethyl ether, THF, 2-Methyl THF, methyl tert.butylether, dimethoxy ethane, cyclopentyl methyl ether and diisopropyl ether. Preferably the solvent is cyclopentyl methylether (CPME). The use of CPME as the solvent in step (d) has advantages over the hazardous, non-ecofriendly chlorinated solvents of the prior art, and results in a high yield and high product purity.

Another advantage of using CPME as the solvent for this reaction is that this reaction can be performed in-situ from the previous Grignard reaction step (step (c)). Thus, the cyanogen bromide reaction (step (d)) can be carried out without isolating the Grignard product of Formula-V.

The subsequent reaction for the preparation of the buprenorphine intermediate of Formula-VII (step (e)) comprises the reaction of the compound of Formula-VI (TARG-NCN) with a base which may be selected from alkali metal hydroxides, for example NaOH, KOH and LiOH, to produce the compound of Formula-VII (TARG-NH).

There is no particular restriction on the nature of the solvent to be employed for the formation of the compound of Formula-VII, provided that it has no adverse effect on the reaction or the reagents involved. Examples of suitable solvents include, but are not limited to, high boiling solvents for example diethylene glycol, triethylene glycol, ethylene glycol, N-methylpyrrolidinone, DMF, DMSO, DMPU, DMA, DEA, water, n-butanol, ethanol and IPA. Preferably the solvent is diethylene glycol. It should be appreciated that the same reaction may be carried out in a biphasic mixture of an organic solvent with water, and a phase transfer catalyst.

Step (e) may be carried out at a temperature of from 160° C. to 170° C. Preferably step (e) is carried out at a temperature of 165° C.

Step (f): N-alkylation to Prepare TARG-NCP (Formula-IX):

Step (f) involves the preparation of the buprenorphine intermediate of Formula-IX, comprising the reaction of the compound of Formula-VII (TARG-NH) with cyclopropyl methyl-L in the presence of a solvent, to produce the compound of Formula-IX (TARG-NCP).

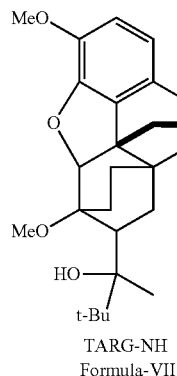

TARG-NH
Formula-VII

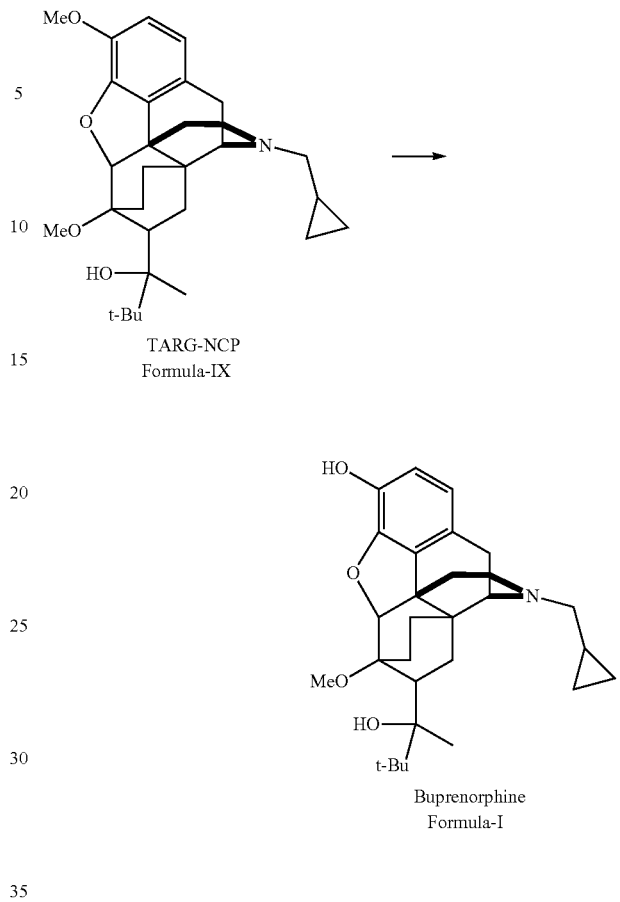

TARG-NCP
Formula-IX

TARG-NCP
Formula-IX

Buprenorphine
Formula-I

The L group in cyclopropyl methyl-L may be a leaving group selected from halides, tosyl and mesyl. The halide leaving group may be chloride, bromide or iodide. Preferably the cyclopropyl methyl-L compound is cyclopropyl methyl bromide.

There is no particular restriction on the nature of the solvent to be employed for the formation of the compound of Formula-IX, provided that it has no adverse effect on the reaction or the reagents involved. Examples of suitable solvents include, but are not limited to, polar aprotic solvents, for example acetonitrile, DMF, DEF, DMSO, N-methylpyrrolidinone, DMPU, DMA, DEA, sulpholane, acetone, methyl ethyl ketone, methyl iso-butyl ketone, THF, Me-THF, CPME, MtBE and DME. Preferably the solvent is acetonitrile or CPME.

The reaction in step (f) may be carried out in the presence of a base or acid scavenger. The base or acid scavenger may be selected from inorganic bases for example alkali and alkaline earth metal carbonates and bicarbonates; and organic bases for example triethylamine, diisopropyl ethyl amine, pyridine, dimethyl amino pyridine, imidazole, ethylene diamine, N,N-dimethyl aniline and colidine. Additionally, KI or NaI may be added in this reaction as a catalyst.

Step (g): O-Demethylation for Preparation of Buprenorphine (Formula-I):

Step (g) involves the preparation of buprenorphine of Formula-I, comprising contacting the compound of Formula-IX (TARG-NCP) with an alkane thiol in the presence of a base and a suitable solvent that enhances the yield and purity of the product buprenorphine.

The alkane thiols selected for this reaction may be straight chain n-alkanethiols, branched chain alkanethiols, alkanethiols containing cyclic rings or dithiols and combinations thereof. The alkanethiols may contain from 5 to 12 carbon atoms. The preferred alkanethiols for this reaction are ethanethiol, pentanethiol, heptanethiol and dodecanethiol.

The base employed in this reaction may be selected from sodium hydride, sodamide and alkali metal C1 to C4 straight chain or branched chain alkoxides. Preferably the base is selected from alkali metal tertiary butoxides. More preferably the base is potassium tertiary butoxide.

The reaction may be carried out at a temperature in the range of from 80° C. to 150° C. Preferably the reaction is carried out at a temperature in the range of from 100° C. to 130° C., more preferably from 110° C. to 115° C.

Examples of suitable solvents for step (g) include, but are not limited to, DMF, DEF, DMSO, toluene and cyclopentyl methyl ether (CPME). Preferably the solvent is DMF or CPME.

Step (g) enables the isolation of the desired product of Formula-I (buprenorphine) in a higher yield and greater purity than the prior art processes, as the reaction is carried out at a comparatively lower temperature with simple work-up and without any extra steps for purification and crystallization.

One specific embodiment of the process of the present invention is shown below in Scheme-4.

Scheme-4:

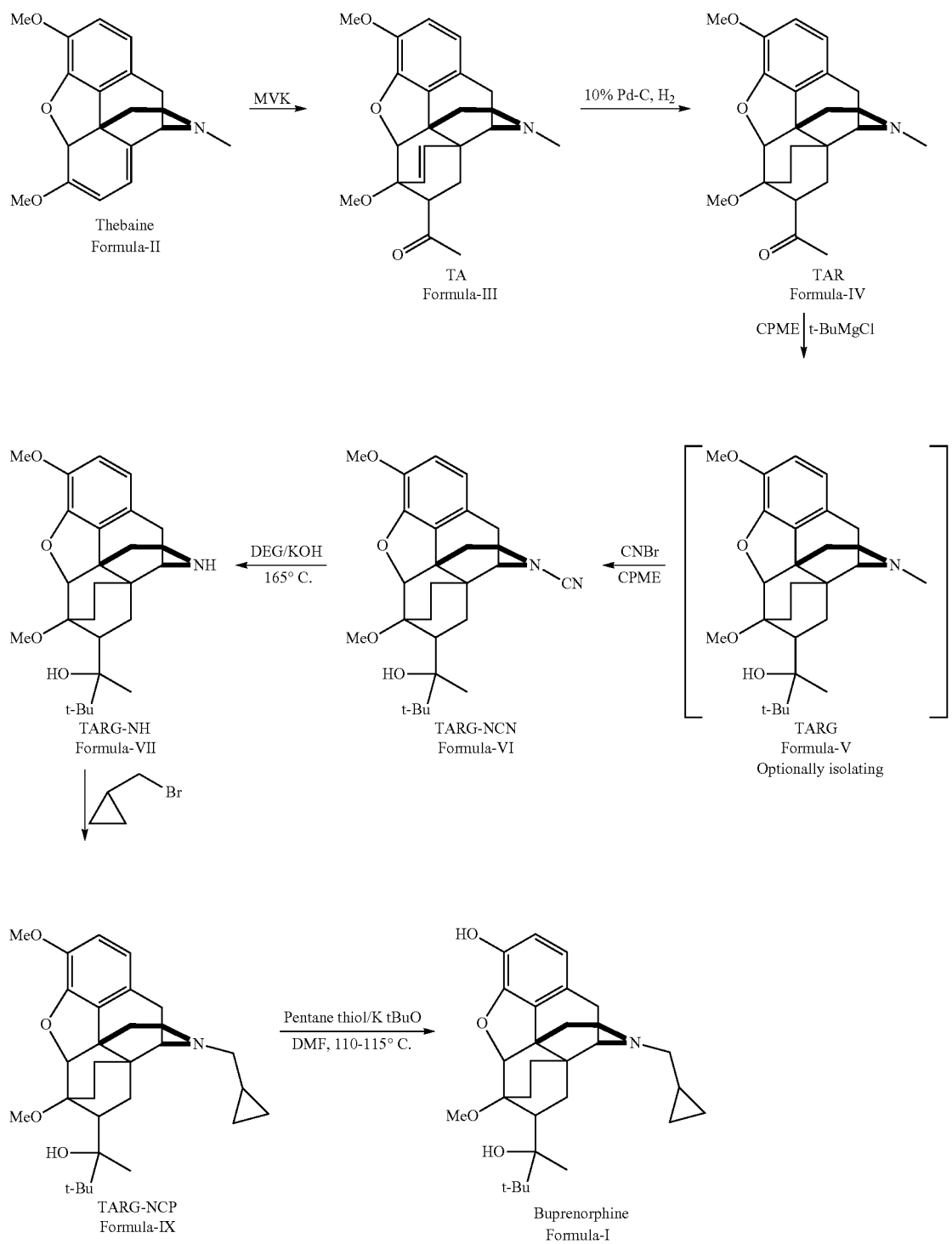

Although the present invention has been described in terms of an overall process for the formation of buprenorphine from thebaine, the invention also relates to each of the individual processes outlined in steps (a) to (g), and to any combination thereof.

According to a second aspect of the present invention, there is provided a process for the preparation of a compound of Formula-V, comprising contacting a compound of Formula-IV with tertiary butyl metal halide in CPME:

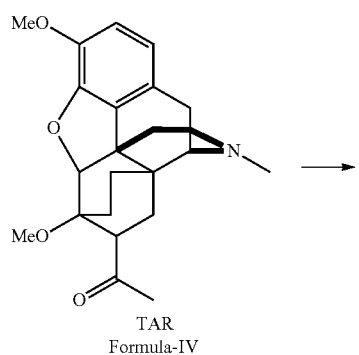

TAR
Formula-IV

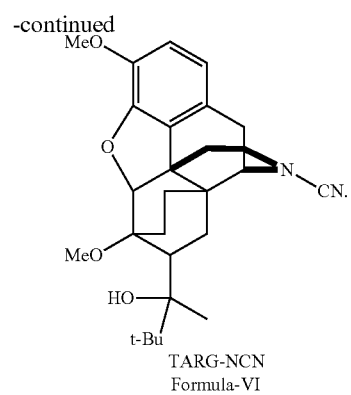

TARG-NCN
Formula-VI

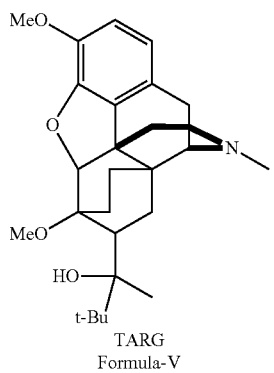

TARG
Formula-V

According to a fourth aspect of the present invention, there is provided a process for the preparation of a compound of Formula-IX, comprising contacting a compound of Formula-VII with cyclopropyl methyl halide in the presence of an acid scavenger in a solvent selected from acetonitrile and CPME, to obtain a compound of Formula-IX:

According to a third aspect of the present invention, there is provided an in-situ process for the preparation of a compound of Formula-VI, comprising contacting a compound of Formula-IV with tertiary butyl metal halide in CPME to obtain a compound of Formula-V, followed by reaction with cyanogen bromide to obtain a compound of Formula-VI, without isolating the compound of Formula-V:

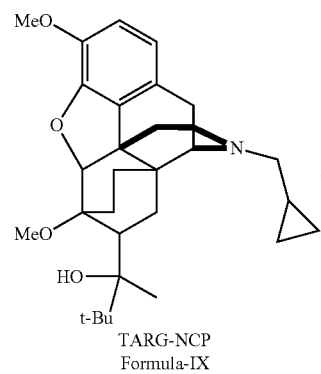

TARG-NH
Formula-VII

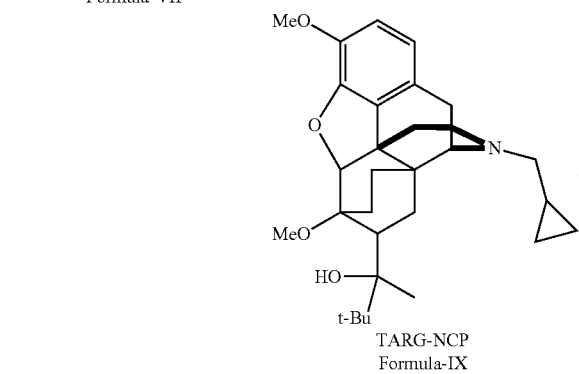

TARG-NCP
Formula-IX

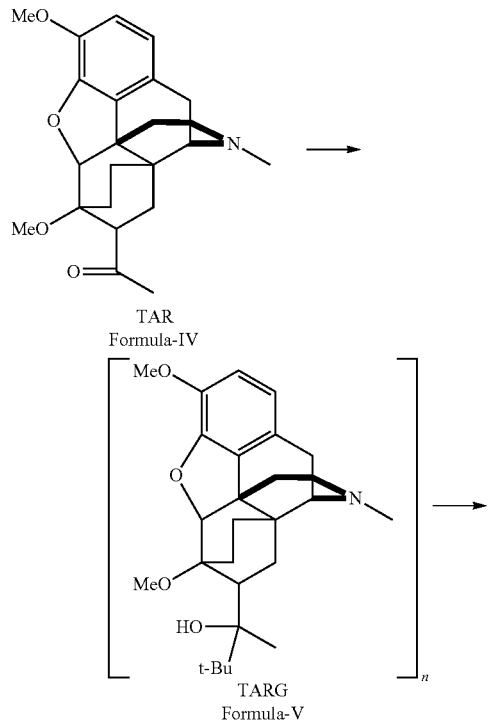

TAR
Formula-IV

TARG
Formula-V

It should be appreciated that the preferred features of the first aspect of the present invention can also relate to the second, third and fourth aspects of the invention.

INDUSTRIAL ADVANTAGES

1. The present invention provides an efficient industrial process which may provide buprenorphine from thebaine in an overall yield of from about 30% to about 50%, more specifically from about 40% to about 42%. This is substantially higher than the prior art yield of 26% to 28% disclosed in US 2011/0152527A1.
2. The loading quantity in step (a) of the hazardous, lachrymatic, toxic and expensive raw material, methyl vinyl ketone, may be reduced to half of its quantity as reported in the prior art process disclosed in US2011/0152527. Additionally, the improved process may produce the thebaine adduct of Formula-III (TA) in a yield of greater than 90%, more specifically from about 91% to about 95%.
3. The present invention may allow for the elimination of diethyl ether, benzene and THF as the reaction media for the Grignard reaction step (step (c)). The use of these solvents is not viable on an industrial scale due to the carcinogenic nature of benzene and the highly flammable and hazardous nature of solvents such as diethyl ether and THF. The inventors of the present invention have surprisingly found that cyclopentyl methyl ether (CPME) can be used as an alternative solvent for this step. CPME has now become available in commercial quantities with approval by the Toxic Substances Control Act (TSCA) and the European List of Notified Chemical Substances (ELINCS). A high boiling point (106° C.) and preferable characteristics such as low formation of peroxides, relative stability under acidic and basic conditions, high hydrophobicity and formation of azeotropes with water, coupled with a narrow explosion range render CPME a favourable alternative to other ethereal solvents such as tetrahydrofuran (THF), 2-methyl tetrahydrofuran (2-MeTHF), dioxane (carcinogenic), and 1,2-dimethoxyethane (DME). The desired product of Formula-V may be obtained with above 99% HPLC purity.
4. In step (d) of the present invention, the reaction of cyanogen bromide is preferably carried out in cyclopentyl methyl ether (CPME) rather than the chlorinated solvents used in the prior art processes. An advantage of using CPME as a solvent in this step is that it enables the reaction to be performed in-situ from the previous step without having to isolate the Grignard reaction product. Thus, the number of operational steps may be reduced.
5. The yield of the compound of Formula-VII from step (d) and step (e) may be as much as 87.4% with HPLC purity above 99%.
6. In the present process, the N-alkylcycloalkylated intermediate of formula-IX is produced in a one-step reaction (step f) of cyclopropyl methyl-L with the compound of Formula-VII (TARG-NH) in the presence of a solvent, for example CPME or acetonitrile, preferably under reflux conditions. Using this process, a yield of 92.9% of the compound of Formula-IX with 99.5% HPLC purity, may be realised.
7. The O-demethylation of step (g) is preferably performed with alkane thiol and potassium tert.

butoxide in DMF at a comparatively lower temperature than the prior art processes. The lower temperature reduces the formation of undesirable impurities, which tend to form when the reaction is performed at a higher temperature, for example between 210° C. and 220° C. Consequently, a higher yield and purity of the final product is achieved.

After completion of the reaction, the reaction mass may be quenched in water and the desired product may be isolated by extraction with CPME or another water immiscible solvent, for example chloroform, MDC or ethyl acetate. The product buprenorphine base may be obtained in a 91% yield with over 99% HPLC purity. Advantageously, no extra step for purification or crystallization is required. The process provides a simpler work-up procedure and results in a substantially higher yield and better quality of the final buprenorphine product than the prior art processes.

8. Contrary to the reports published in WO 2013/050748, the inventors of the present invention have successfully performed the 3-O-demethylation on the compound of Formula-IX (the N-methylcyclopropyl substituted intermediate), with high yield and purity. The chance of impurity formation which arises when the intermediate of formula-IX is alkylated (as alkylation may occur on both the amine and 3-phenolic position), is reduced in the present process. Thus, the process results in a higher yield and better quality of the final product.

The invention will now be more specifically described by the following examples, so that various aspects thereof may be more fully understood and appreciated.

Example 1

Preparation of TA of Formula-III 50 kg of thebaine was added to 100 L dry toluene, and the mixture was cooled to 15° C. 25 L of MVK was added to the cooled mixture and stirred for 30 minutes, followed by stirring at 80° C. to 85° C. for 18 hours. The solvent was removed under reduced pressure and the residual mass was stripped off with isopropyl alcohol, cooled to room temperature and stirred for 1 hour. The resultant product was isolated and dried to get 57.01 kg product TA (Yield: 93.28%; HPLC purity: 99%).

Example 2

Preparation of TAR of Formula-IV

60 L of isopropanol, 6 kg of TA and 250 g of 10% Pd—C catalyst were charged into a 100 L autoclave and hydrogenated at 100 PSI for 3 to 4 hours at 80° C. to 85° C. The charcoal was filtered off under hot conditions and the solvent was partially removed, the remaining mixture was cooled to room temperature and stirred for 2 hours. Finally, the product was filtered to get 5.58 kg TAR (Yield: 92.53%; HPLC purity: 99.5%).

Example 3

Preparation of TARG of Formula-V

Under an inert atmosphere and anhydrous conditions, 1 kg of magnesium turnings and iodine was charged into a vessel. To this was added 3.5 L of CPME. 1 L of t-butyl chloride was added to the mixture under stirring. The mixture was heated slowly and maintained below reflux temperature, until the reaction started. A further 5 L of t-butyl chloride and 30 L of CPME was added to the reaction mixture at such a rate that reaction did not subside. After the addition was completed, the reaction mixture was stirred for 12 hours at 35° C. to 40° C. 1 kg of TAR in CPME was added to the reaction mixture and stirred at 35° C. to 40° C. for 10 hours. The reaction mixture was cooled and quenched with ammonium chloride in 70 L of water. Suitable work up gave 710 g TARG (Yield: 61.18%; HPLC purity: 98.74%).

Same Reaction Scaled-Up to 10 Kg:

10 kg of magnesium turnings and iodine was charged into a 1000 L vessel under an inert atmosphere and anhydrous conditions. To this was added 35 L of CPME. 1 L of t-butyl chloride was added to the mixture under stirring. The mixture was heated slowly and maintained below reflux temperature, until the reaction started. A further 50 L of t-butyl chloride and 300 L of CPME was added to the reaction mixture at such a rate that the reaction did not subside. After the addition was completed, the reaction mixture was stirred for 12 hours at 35° C. to 40° C. 10 kg of TAR in CPME was added to the reaction mixture and stirred at 35° C. to 40° C. for 10 hours. The reaction mixture was cooled and quenched with ammonium chloride in 700 L of water. Suitable work-up gave 7.5 kg TARG (Yield: 65.16%; HPLC purity: 99.09%).

Example 4

Preparation of TARG-NCN of Formula-VI 5 kg of TARG was dissolved in 15 L CPME. To this was added 1.4 kg of cyanogen bromide. The reaction mixture was stirred under reflux conditions until completion of the reaction. The solvent was removed under reduced pressure, stripped off with methanol, cooled and then filtered to obtain 4.815 kg of product TARG-NCN (Yield: 93.95%; HPLC purity: 99.5%).

Example 5

Preparation of TARG-NCN from TAR In-Situ

Under an inert atmosphere and anhydrous conditions, 1 kg of magnesium turnings and iodine was charged into a vessel. To this was added 10 L of CPME. 0.1 L of t-butyl chloride was added to the reaction mixture under stirring until the reaction started. A further 0.5 L of t-butyl chloride and 30 L of CPME was added to the reaction mixture at such a rate that the reaction did not subside. After the addition was completed, the reaction mixture was stirred at 35° C. to 40° C. until completion of the reaction. 1 kg of TAR in CPME was added to the reaction mixture and stirred at 35° C. to 40° C. until completion of the reaction. The reaction mixture was cooled and worked up as in Example 3 to obtain TARG in CPME. To this was added 0.2 kg cyanogen bromide and the reaction mixture was stirred under reflux conditions until completion of reaction. The solvent was removed under reduced pressure, stripped off with methanol, cooled and filtered to get 0.72 kg of product TARG-NCN.

Example 6

Preparation of TARG-NH of Formula-VII 6.0 kg of TARG-NCN was taken in 52 L of diethylene glycol and 4.8 kg potassium hydroxide. The reaction mixture was stirred at 165° C. until completion of the reaction. The reaction mass was cooled and placed in water. This mixture was stirred at 15° C. to 20° C. for 2 to 3 hours. The solid was filtered off and dried to obtain 5.24 kg of product TARG-NH (Yield: 92.94%; HPLC purity: 99%)

Example 7

Preparation of TARG-NCP of Formula-IX 5 kg TARG-NH was taken in 35 L acetonitrile and the reaction mass cooled. To this was added 4.54 kg anhydrous potassium carbonate, followed by the addition of 1.775 kg cyclopropyl methyl bromide. The reaction mixture was stirred under reflux conditions until completion of the reaction. The unwanted material was filtered off and the filtrate was distilled to reduce the quantity and cooled to obtain 5.23 kg of product TARG-NCP; (Yield: 92.89%; HPLC purity: 99.5%).

The same reaction was performed using CPME as the solvent to get the product (TARG-NCP) in an equivalent yield and purity.

Example 8

(a) Preparation of Buprenorphine (BPN) using Pentanethiol*

100 L DMF was charged into a vessel under an inert atmosphere. To this was added 3.6 L pentane thiol. The mixture was stirred and then 3.6 kg of potassium t-butoxide was added in batches. 3 kg of TARG-NCP was added to the mixture and subsequently the reaction mixture was stirred at 100° C. to 130° C. for 18 hours. The reaction mixture was cooled and placed in water containing ammonium chloride. The aqueous layer was extracted with CPME/chloroform to give 2.654 kg buprenorphine (Yield: 91%; HPLC purity: 99.22%).

* This reaction is also carried out on 14 kg input scale, by changing sequence of addition, giving satisfactory yield.

(b) Preparation of Buprenorphine (BPN) Using Heptanethiol 100 ml DMF was charged into a vessel under an inert atmosphere. To this was added 10 ml heptanethiol. The mixture was stirred and then 10 g potassium t-butoxide was added. 5 g TARG-NCP was further added to the mixture and subsequently the reaction mixture was stirred at 100° C. to 130° C. for 16 hours. The reaction mixture was cooled and placed in 750 ml water containing ammonium chloride. The aqueous layer was extracted with CPME/chloroform to obtain 3.806 g buprenorphine (Yield: 78.40%; HPLC purity 99%).

(c) Preparation of Buprenorphine (BPN) Using Ethanethiol

1 L of DMF was added to 50 ml of ethanethiol under an inert atmosphere and stirred. To this was added 51 g of potassium t-butoxide. 25 g of TARG-NCP was added to the mixture and the reaction mixture was stirred at 100° C. to 13° C. for 18 hours. The reaction mixture was placed into water containing ammonium chloride and extracted with chloroform/CPME to get 20.31 g buprenorphine (Yield: 83.68%; HPLC purity: 98.92%).

(d) Preparation of Buprenorphine (BPN) using Dodacanethiol 200 ml of DMF was charged into a vessel under an inert atmosphere. To this was added 80 ml of dodacanethiol. The mixture was stirred followed by addition of 80 g of potassium t-butoxide. 10 g TARG-NCP was added to the mixture and subsequently the reaction mixture was stirred at 100° C. to 130° C. for 16 hours. The reaction mixture was cooled and placed in water containing ammonium chloride. The aqueous layer was extracted with CPME/chloroform to obtain buprenorphine (HPLC purity: 77%).

(e) Preparation of Buprenorphine (BPN) Using Sodium t-Butoxide

The potassium salt of pentanethiol (6.61 g; prepared from pentanethiol & potassium t-butoxide) was charged into a vessel containing 75 ml DMF under inert atmosphere. To this solution was added 5 g TARG-NCP. The reaction mixture was stirred at 100-130° C. for 4 hours. The reaction mixture was cooled and placed in 225 ml water containing ammonium chloride. The aqueous layer was extracted with CPME to obtain 2.98 g buprenorphine (Yield: 61%; HPLC purity 98.57%).

(f) Preparation of Buprenorphine (BPN) Using Sodium t-Butoxide

DMF (150 ml) was charged under inert atmosphere into a vessel. To this vessel was added 12 g sodium t-butoxide. The resulting solution was stirred, followed by addition of 12 mL pentanethiol to the stirred solution. To the resulting mixture was further added 10 g TARG-NCP, and the reaction mixture was stirred at 100-130° C. for 6 hours. The reaction mixture was cooled and placed in 600 ml water containing ammonium chloride. The aqueous layer was extracted with CPME/chloroform to obtain 7.08 g buprenorphine (Yield: 72.9%; HPLC purity 98.05%).

(g) Preparation of Buprenorphine (BPN) Using N,N-Dimethyl Acetamide as Solvent

N,N-dimethyl acetamide (150 ml) was charged under inert atmosphere into a vessel. To this vessel was added 12 g potassium t-butoxide. The resulting solution was stirred, followed by addition of 12 mL pentanethiol. To the resulting mixture was further added 10 g TARG-NCP, and the reaction mixture was stirred at 100-130° C. for 6 hours. The reaction mixture was cooled and placed in 600 ml water containing ammonium chloride. The aqueous layer was extracted with CPME/chloroform to obtain 7 g buprenorphine (Yield: 72.1%; HPLC purity 98.22%)

The invention claimed is:

1. A process for the preparation of a compound of Formula-I in a purity of at least 98%, comprising:

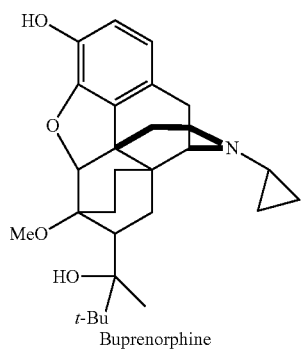

Formula-I
Buprenorphine contacting a compound of Formula-IX with a $C_2$-$C_7$ alkanethiol and a base in a first solvent to produce a compound of Formula-I, wherein said first solvent is DMF:

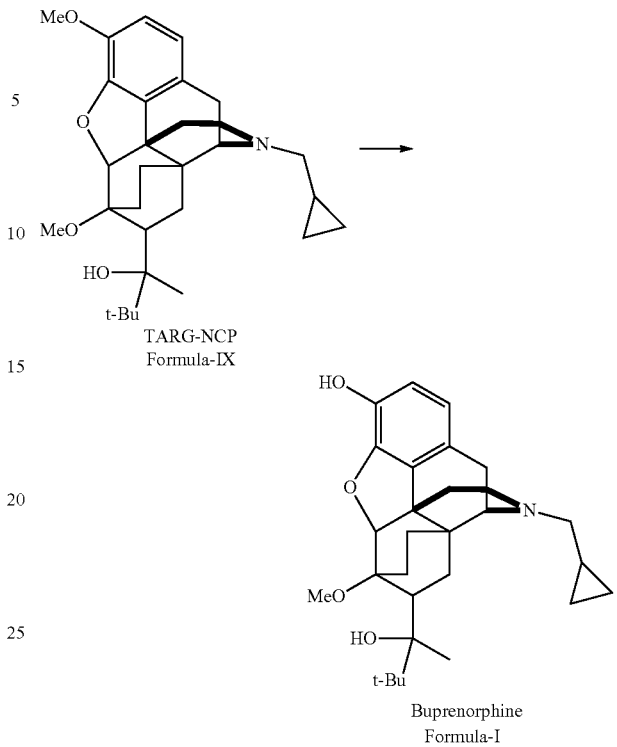

TARG-NCP
Formula-IX

Buprenorphine
Formula-I said contacting being carried out at a temperature between about 80° C. and about 150° C.

2. The process according to claim 1, wherein the alkanethiol is selected from the group consisting of straight chain n-alkanethiols, branched chain alkanethiols, cyclic alkanethiols, dithiols, alkali metal salts thereof, and mixtures thereof.

3. The process according to claim 1, wherein the alkanethiol is at least one alkanethiol selected from the group consisting of straight chain n-alkanethiols containing from 5 to 7 carbon atoms.

4. The process according to claim 1, wherein the alkanethiol is selected from the group consisting of ethanethiol, pentanethiol, heptanethiol, and mixtures thereof.

5. The process according to claim 1, wherein the compound of Formula-IX is obtained by contacting a compound of Formula-VII with a cyclopropyl methyl halide, cyclopropyl methyl tosylate, or cyclopropyl methyl mesylate in a second solvent to produce the compound of Formula-IX:

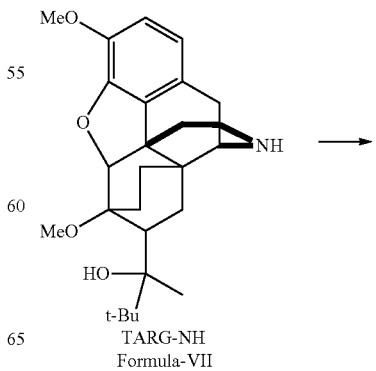

TARG-NH
Formula-VII

6. The process according claim 5, wherein said second solvent is a polar aprotic solvent.

7. The process according to claim 6, wherein the polar aprotic solvent is selected from the group consisting of acetonitrile, DMF, DEF, DMSO, N-methylpyrrolidinone, DMPU, DMA, DEA, sulpholane, acetone, methyl ethyl ketone, methyl isobutyl ketone, THF, Me-THF, dioxane, CPME, MtBE, and DME.

8. The process according to claim 5, wherein the compound of Formula-VII is obtained by a) contacting a compound of Formula-V with cyanogen bromide in a third solvent to yield a compound of Formula-VI; and b) contacting the compound of Formula-VI with an alkali metal hydroxide in a fourth solvent to obtain the compound of Formula-VII:

9. The process according to claim 8, wherein the third solvent is an ethereal solvent.

10. The process according to claim 9, wherein the ethereal solvent is selected from the group consisting of diethyl ether, tetrahydrofuran; 2-methyl tetrahydrofuran, methyl tert-butylether, dimethoxyethane, cyclopentyl methyl ether and diisopropyl ether.

11. The process according to claim 8, wherein the compound of Formula-V is obtained by contacting a compound of Formula-IV with a tertiary butyl metal halide in a fifth solvent to obtain the compound of Formula-V:

12. The process according to claim 11, wherein the tertiary butyl metal halide is selected from the group consisting of tertiary butyl magnesium halide, tertiary butyl lithium halide, tertiary butyl zinc halide, and tertiary butyl cadmium halide.

13. The process according to claim 11, wherein the fifth solvent is selected from the group consisting of dialkyl ether, wherein alkyl is selected from the group consisting of C1 to C4 straight chain or branched chain alkyl groups; tetrahydrofuran; 2-methyl tetrahydrofuran; cyclopentyl methyl ether; dioxanes; dialkoxyethane; hydrocarbons selected from the group consisting of toluene, hexane, and heptane; and mixtures thereof.

14. The process according to claim 11, wherein the fifth solvent comprises cyclopentyl methyl ether.

15. The process according to claim 11, wherein the compound of Formula-IV is obtained by:
c) reacting thebaine of Formula-II with methyl vinyl ketone in a sixth solvent to obtain a compound of Formula-III; and

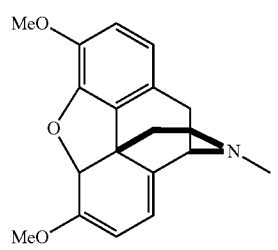

Thebaine
Formula-II

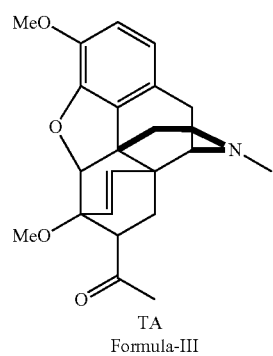

TA
Formula-III d) reducing the compound of Formula-III by catalytic hydrogenation or by a catalytic transfer hydrogenation reaction in a seventh solvent to obtain the compound of Formula-IV:

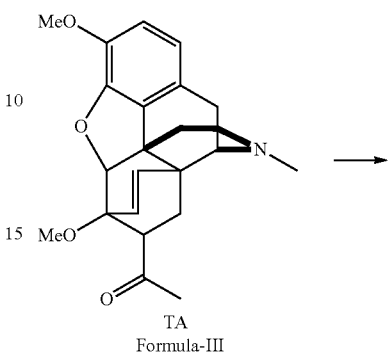

TA
Formula-III

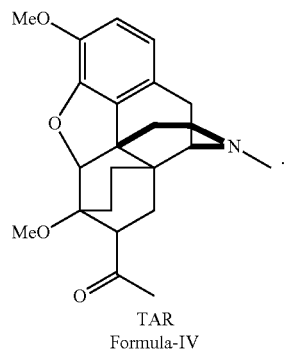

TAR
Formula-IV

16. The process according to claim 15, wherein 0.5 liters methyl vinyl ketone are used per kg thebaine in step (c).

17. The process according to claim 15, wherein the sixth and seventh solvents are the same or different; and
wherein the sixth and seventh solvents are each selected from the group consisting of toluene, IPA, cyclopentyl methyl ether, and mixtures thereof.

* * * * *